(12) United States Patent
Wilson et al.

(10) Patent No.: US 11,266,391 B2
(45) Date of Patent: Mar. 8, 2022

(54) SURGICAL RETRACTOR AND METHOD

(71) Applicant: Warsaw Orthopedic, Inc., Warsaw, IN (US)

(72) Inventors: Madeline G. Wilson, Memphis, TN (US); Mladen Djurasovic, Louisville, KY (US); Charles Hopkins Crawford, III, Prospect, KY (US); Jeffrey Lynn Gum, Crestwood, KY (US); Roger Kirk Owens, II, Prospect, KY (US)

(73) Assignee: Warsaw Orthopedic, Inc., Warsaw, IN (US)

(*) Notice: Subject to any disclaimer, the term of this patent is extended or adjusted under 35 U.S.C. 154(b) by 364 days.

(21) Appl. No.: 16/272,640

(22) Filed: Feb. 11, 2019

(65) Prior Publication Data
US 2020/0253594 A1 Aug. 13, 2020

(51) Int. Cl.
*A61B 17/02* (2006.01)
*A61B 34/30* (2016.01)
*A61B 90/50* (2016.01)
*A61B 17/70* (2006.01)
*A61B 17/90* (2006.01)

(52) U.S. Cl.
CPC ...... *A61B 17/0206* (2013.01); *A61B 17/7074* (2013.01); *A61B 17/90* (2021.08)

(58) Field of Classification Search
CPC ............ A61B 17/0206; A61B 17/0218; A61B 17/7074; A61B 34/30; A61B 90/50; A61B 2017/00477; A61B 2017/90
USPC ................................................. 600/201–249
See application file for complete search history.

(56) References Cited

U.S. PATENT DOCUMENTS

| 20,905 | A | * | 7/1858 | Thomas | A61B 1/24 600/238 |
| 1,706,500 | A | | 3/1929 | Smith | |
| 1,707,689 | A | * | 4/1929 | Sloan | A61B 17/0293 600/233 |
| 1,963,173 | A | * | 6/1934 | Morin | A61B 17/0293 600/233 |
| 2,698,795 | A | | 11/1954 | Greishaber | |
| 3,626,471 | A | | 12/1971 | Florin | |
| 3,965,890 | A | | 6/1976 | Gauthier | |
| 4,344,420 | A | * | 8/1982 | Forder | A61B 17/0206 600/232 |
| 4,718,151 | A | | 1/1988 | LeVahn et al. | |
| 5,027,793 | A | | 7/1991 | Englehart et al. | |
| 5,080,088 | A | * | 1/1992 | LeVahn | A61B 17/02 600/206 |
| 5,299,563 | A | * | 4/1994 | Seton | A61B 17/0293 128/898 |

(Continued)

FOREIGN PATENT DOCUMENTS

| EP | 0951868 | 10/1999 |
| WO | 2015054070 | 4/2015 |

*Primary Examiner* — Jessica Weiss
(74) *Attorney, Agent, or Firm* — Sorell, Lenna & Schmidt, LLP

(57) ABSTRACT

A surgical retractor comprises at least one blade including a first arm and a second arm spaced apart from the first arm. The at least one blade further including a member being disposed with the arms to support at least one surgical instrument in a selected orientation relative to a surgical site. Surgical systems, instruments, constructs, implants and methods are disclosed.

20 Claims, 15 Drawing Sheets

(56) References Cited

U.S. PATENT DOCUMENTS

| | | | |
|---|---|---|---|
| 5,363,841 | A * | 11/1994 | Coker .................. A61B 17/0206 600/211 |
| 5,365,921 | A * | 11/1994 | Bookwaiter ....... A61B 17/0206 269/261 |
| 5,727,899 | A | 3/1998 | Dobrovolny |
| 5,928,139 | A | 7/1999 | Koros et al. |
| 5,957,835 | A * | 9/1999 | Anderson .............. A61B 17/12 600/201 |
| 6,051,007 | A | 4/2000 | Hogendijk et al. |
| 6,074,343 | A | 6/2000 | Nathanson et al. |
| 6,102,854 | A * | 8/2000 | Cartier .................... A61B 1/32 600/210 |
| 6,206,826 | B1 | 3/2001 | Matthews et al. |
| 6,322,500 | B1 | 11/2001 | Sikra et al. |
| 6,345,946 | B1 | 2/2002 | Manini et al. |
| 6,416,469 | B1 | 7/2002 | Phung et al. |
| 6,458,079 | B1 * | 10/2002 | Cohn ..................... A61B 17/02 600/213 |
| 6,468,207 | B1 * | 10/2002 | Fowler, Jr. ......... A61B 17/0206 600/217 |
| 6,500,116 | B1 * | 12/2002 | Knapp ............... A61B 17/0206 600/210 |
| 6,599,240 | B2 | 7/2003 | Puchovsky et al. |
| 7,033,377 | B2 | 4/2006 | Miller, III |
| 7,097,616 | B2 | 8/2006 | Bjork et al. |
| 7,125,380 | B2 | 10/2006 | Yager |
| 7,207,949 | B2 | 4/2007 | Miles et al. |
| 7,404,792 | B2 * | 7/2008 | Spence .................. A61B 17/02 600/37 |
| 7,513,869 | B2 | 4/2009 | Branch et al. |
| 7,594,888 | B2 | 9/2009 | Raymond et al. |
| 7,618,431 | B2 | 11/2009 | Roehm, III |
| 7,691,057 | B2 | 4/2010 | Miles et al. |
| 7,785,253 | B1 | 8/2010 | Arambula et al. |
| 7,803,176 | B2 | 9/2010 | Teague et al. |
| 7,892,173 | B2 | 2/2011 | Miles et al. |
| 7,905,840 | B2 | 3/2011 | Pimenta et al. |
| 7,909,846 | B1 * | 3/2011 | Taylor ................. A61B 17/3423 606/198 |
| 7,920,922 | B2 | 4/2011 | Gharib et al. |
| 7,935,051 | B2 | 5/2011 | Miles et al. |
| 7,962,191 | B2 | 6/2011 | Marino et al. |
| 7,981,029 | B2 | 7/2011 | Branch et al. |
| 8,000,782 | B2 | 8/2011 | Gharib et al. |
| 8,005,535 | B2 | 8/2011 | Gharib et al. |
| 8,016,767 | B2 | 9/2011 | Miles et al. |
| 8,038,611 | B2 | 10/2011 | Raymond et al. |
| 8,047,987 | B2 | 11/2011 | Grey et al. |
| 8,055,349 | B2 | 11/2011 | Gharib et al. |
| 8,062,217 | B2 | 11/2011 | Boucher et al. |
| 8,062,218 | B2 | 11/2011 | Sebastian et al. |
| D652,519 | S | 1/2012 | Miles et al. |
| D652,921 | S | 1/2012 | Miles et al. |
| D652,922 | S | 1/2012 | Miles et al. |
| 8,114,019 | B2 | 2/2012 | Miles et al. |
| 8,133,173 | B2 | 3/2012 | Miles et al. |
| 8,137,284 | B2 | 3/2012 | Miles et al. |
| 8,165,653 | B2 | 4/2012 | Marino et al. |
| 8,172,750 | B2 | 5/2012 | Miles et al. |
| 8,182,423 | B2 | 5/2012 | Miles et al. |
| 8,187,179 | B2 | 5/2012 | Miles et al. |
| 8,192,356 | B2 | 6/2012 | Miles et al. |
| 8,192,357 | B2 | 6/2012 | Miles et al. |
| D666,292 | S | 8/2012 | Miles et al. |
| D666,923 | S | 8/2012 | Miles et al. |
| D666,924 | S | 8/2012 | Miles et al. |
| 8,244,343 | B2 | 8/2012 | Gharib et al. |
| 8,303,498 | B2 | 11/2012 | Miles et al. |
| 8,343,046 | B2 | 1/2013 | Miles et al. |
| 8,353,826 | B2 | 1/2013 | Weiman |
| 8,357,184 | B2 | 1/2013 | Woolley et al. |
| 8,579,809 | B2 | 11/2013 | Parker |
| 8,636,655 | B1 | 1/2014 | Childs |
| 8,657,819 | B2 | 2/2014 | Murner et al. |
| 8,882,662 | B2 | 11/2014 | Charles |
| 9,044,280 | B1 | 6/2015 | Arambula et al. |
| 9,138,217 | B2 | 9/2015 | Smith et al. |
| 2004/0176665 | A1 | 9/2004 | Branch et al. |
| 2006/0224044 | A1 | 10/2006 | Marchek et al. |
| 2007/0161865 | A1 * | 7/2007 | Fakhrai .............. A61B 17/0206 600/231 |
| 2007/0203400 | A1 * | 8/2007 | Santilli .............. A61B 17/0293 600/234 |
| 2007/0208227 | A1 | 9/2007 | Smith et al. |
| 2007/0293729 | A1 | 12/2007 | Grey et al. |
| 2008/0077171 | A1 * | 3/2008 | Blain ................. A61B 17/0206 606/190 |
| 2008/0108877 | A1 * | 5/2008 | Bayat ...................... A61B 1/32 600/214 |
| 2008/0132766 | A1 | 6/2008 | Dant et al. |
| 2009/0118774 | A1 | 5/2009 | Miller, III |
| 2009/0287060 | A1 * | 11/2009 | Pell ..................... A61M 5/1407 600/201 |
| 2011/0046448 | A1 | 2/2011 | Paolitto et al. |
| 2012/0010472 | A1 | 1/2012 | Spann |
| 2012/0088979 | A1 * | 4/2012 | Nunley .............. A61B 17/0206 600/231 |
| 2012/0245431 | A1 | 9/2012 | Baudouin et al. |
| 2012/0283521 | A1 | 11/2012 | Smith et al. |
| 2013/0103103 | A1 | 4/2013 | Mire et al. |
| 2013/0190575 | A1 | 7/2013 | Mast et al. |
| 2013/0274557 | A1 | 10/2013 | Bowman et al. |
| 2014/0039267 | A1 * | 2/2014 | Seex ..................... A61B 90/06 600/206 |
| 2014/0066719 | A1 * | 3/2014 | Nichter .................. A61B 17/02 600/215 |
| 2014/0135584 | A1 | 5/2014 | Lee et al. |
| 2015/0088030 | A1 | 3/2015 | Taylor |
| 2015/0099939 | A1 * | 4/2015 | Beck ..................... A61B 17/02 600/214 |
| 2015/0100129 | A1 | 4/2015 | Waugh et al. |
| 2016/0151058 | A1 * | 6/2016 | Ferro ..................... A61B 17/02 600/215 |

\* cited by examiner

SURGICAL RETRACTOR AND METHOD

TECHNICAL FIELD

The present disclosure generally relates to medical devices for the treatment of musculoskeletal disorders, and more particularly to a surgical system and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, correction, discectomy, laminectomy, corpectomy and implantable prosthetics. As part of these surgical treatments, spinal constructs, such as, for example, bone fasteners, spinal rods and interbody devices can be used to provide stability to a treated region. For example, during surgical treatment, surgical instruments can be used to deliver components of the spinal constructs to the surgical site for fixation with bone to immobilize a joint. Surgical retractors may be employed during a surgical treatment to provide access and visualization of a surgical site. Such retractors space apart and support tissue and/or other anatomical structures to expose anatomical structures adjacent the surgical site and/or provide a surgical pathway to the surgical site. This disclosure describes an improvement over these prior technologies.

SUMMARY

In some embodiments, a surgical retractor is provided. The surgical retractor comprises at least one blade including a first arm and a second arm spaced apart from the first arm. The at least one blade further includes a member being disposed with the arms to support at least one surgical instrument in a selected orientation relative to a surgical site. In some embodiments, surgical systems, instruments, constructs, implants and methods are disclosed.

In some embodiments, the surgical retractor comprises a first blade including spaced apart arms being connected via a member. The member and the arms are relatively disposed in a configuration to guide at least one surgical instrument in a selected orientation relative to a surgical site. A second blade is movable relative to the first blade. The second blade includes spaced apart arms being connected via a member. The member and the arms of the second blade are relatively disposed in a configuration to guide at least one surgical instrument in a selected orientation relative to the surgical site.

In some embodiments, a surgical system is provided. The surgical system comprises at least one blade including a first arm and a second arm spaced apart from the first arm. The at least one blade further includes a member disposed with the arms and defining an opening. A retraction rack is connected with the at least one blade. At least one surgical instrument is supported by the member and disposable within the opening in a selected orientation relative to a surgical site.

BRIEF DESCRIPTION OF THE DRAWINGS

The present disclosure will become more readily apparent from the specific description accompanied by the following drawings, in which.

DETAILED DESCRIPTION

Figure 1:
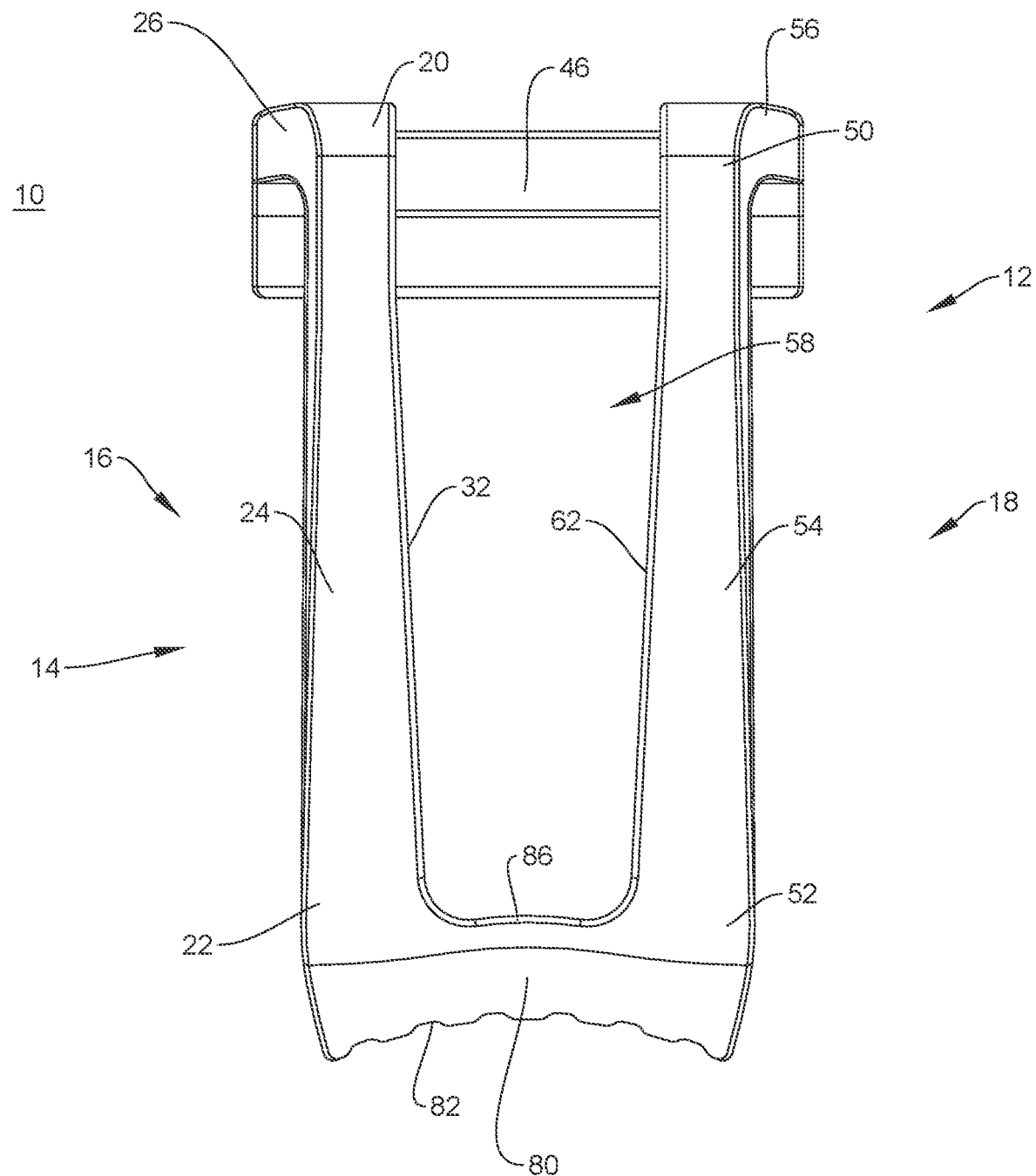
FIG. 1 is a side view of components of one embodiment of a surgical system in accordance with the principles of the present disclosure.

The exemplary embodiments of the surgical system and related methods of use disclosed are discussed in terms of medical devices for the treatment of musculoskeletal disorders and more particularly, in terms of a surgical system for accessing a spine to facilitate treatment thereof and a method for treating a spine. In some embodiments, the systems and methods of the present disclosure comprise one or more retractor blades that are configured to provide selective orientation and positioning of surgical instrumentation and/or support of patient anatomy. In some embodiments, the retractor blade includes surfaces and/or openings to provide selective orientation and positioning of surgical instrumentation and/or support of patient anatomy. In some embodiments, the retractor blade includes a cutout that provides instrumentation and anatomical relief.

In some embodiments, the present surgical system comprises a surgical instrument, for example, a surgical retractor blade configured to facilitate a contralateral decompression and/or a discectomy during a midline posterior thoracolumbar approach by allowing posterior instrumentation to be angulated laterally as well as cephalad-caudally via surfaces and/or openings of the surgical retractor blade, for example, surfaces defining a cutout, while maintaining retraction of soft tissue out of a working surgical field. In some embodiments, the cutout provides for anatomical relief to facilitate an increase of insertion of the retractor into a patient body adjacent to the working surgical field without impinging on the facets or the transverse processes. In some embodiments, the cut out includes an arcuate configuration. In some embodiments, the cut out includes a square configuration.

In some embodiments, the present surgical system comprises a surgical retractor blade including a surface that defines an opening in a front plane and/or a top plane of the blade to facilitate manipulation of one or more surgical instruments. In some embodiments, the surface openings in the front plane and/or the top plane of the blade allow the one or more surgical instruments to be angulated laterally and/or cephalad-caudally, while distal surface openings of the blade allow for anatomical relief, for example, along a midline lumbar fusion (MIDLF) surgical approach.

In some embodiments, the present surgical system comprises a surgical retractor blade including a surface that defines teeth disposed in an arcuate configuration and/or a rectangular cutout that provides anatomical relief and allows the blade to be disposed in the working surgical field and/or wound without impinging on the facets or the transverse processes. In some embodiments, the present surgical system comprises a surgical retractor blade including a surface that defines a large cutout in a front plane and/or a top plane of the blade to allow for instrumentation to be angulated up to approximately 30 degrees medial-laterally, as well as up to 20 degrees in the cephalad-caudal direction, respectively. In some embodiments, the surgical retractor blade facilitates a contra-lateral decompression and discectomy during a midline posterior transforaminal lumbar (TL) surgical approach, while decreasing surgical procedure duration.

In some embodiments, the present surgical system can be employed with a method for treating a spine including the step of connecting and/or slidably engaging one or more surgical retractor blades with a mating retraction rack. In some embodiments, the method includes the step of manipulating the retraction rack to laterally translate the blades. In some embodiments, the method includes the step of manipulating and/or drawing the blades into tension, thereby retracting an incision in the working surgical field.

In some embodiments, the present surgical system comprises a surgical retractor blade including a surface that defines an arc or cutout on a distal end thereof to provide anatomical relief, which allows the blade to be disposed in the working surgical field and/or wound at a selected depth. In some embodiments, this configuration allows surgical instrumentation to be angulated and disposed through the cutout, which opens a working space in the working surgical field and/or wound to facilitate the procedure, for example, a discectomy. In some embodiments, the present surgical system comprises a surgical retractor blade that can be manufactured via an additive manufacturing process, for example, 3D printing.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-5, there are illustrated components of a surgical system 10.

The components of surgical system 10 can be fabricated from biologically acceptable materials suitable for medical applications, including metals, synthetic polymers, ceramics and bone material and/or their composites. For example, the components of surgical system 10, individually or collectively, can be fabricated from materials such as stainless steel alloys, commercially pure titanium, titanium alloys, Grade 5 titanium, super-elastic titanium alloys, cobaltchrome alloys, stainless steel alloys, super elastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyimide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as hydroxyapatite (HA), corraline HA, biphasic calcium phosphate, tricalcium phosphate, or fluorapatite, tri-calcium phosphate (TCP), HA-TCP, calcium sulfate, or other resorbable polymers such as polyaetide, polyglycolide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-β), osteoblast cells, growth and differentiation factor (GDF), insulin-like growth factor 1, platelet-derived growth factor, fibroblast growth factor, or any combination thereof.

Various components of surgical system 10 may have material composites, including the above materials, to achieve various desired characteristics such as strength, rigidity, elasticity, compliance, biomechanical performance, durability and radiolucency or imaging preference. The components of surgical system 10, individually or collectively, may also be fabricated from a heterogeneous material such as a combination of two or more of the above-described materials. The components of surgical system 10 may be monolithically formed, integrally connected or include fastening elements and/or instruments, as described herein.

Surgical system 10 includes a surgical instrument, such as, for example, a surgical retractor 12 (FIG. 4) having a pair of retractor blades, such as, for example, blade 14 and blade 14a, similar to blade 14 described herein. Blade 14 is configured to provide selective orientation and positioning of a surgical instrument and/or support of patient anatomy. Blade 14 includes surfaces and/or openings to provide the selective orientation and positioning of the surgical instrument and/or support of the patient anatomy, as described herein. For example, blade 14 is configured to support and/or provide limitation of movement of a surgical instrument in a selected orientation relative to a surgical site, such as, for example, angulation of a surgical instrument in medial-lateral orientation and/or a cephalad-caudad orientation during a midline thoracolumbar approach. In some embodiments, surgical retractor 12 may include one or a plurality of blades 14.

Blade 14 includes an arm 16 and an arm 18 being spaced apart from arm 16, as shown in FIG. 1. Arm 16 includes a portion 24 and a portion 26. Portion 24 extends between an end 20 and an end 22 along an axis X1 in a plane P1. In some embodiments, plane P1 is disposed a cephalad-caudad orientation relative to a patient body B. Portion 24 includes a surface 30 configured for engaging and spacing apart tissue. Portion 24 includes a surface 32 extending along axis X1 in plane P1. Surface 32 provides a limit to and/or restricts a range of movement of a surgical instrument to facilitate selective orientation and positioning of the surgical instrument within plane P1, as described herein.

Figure 2:
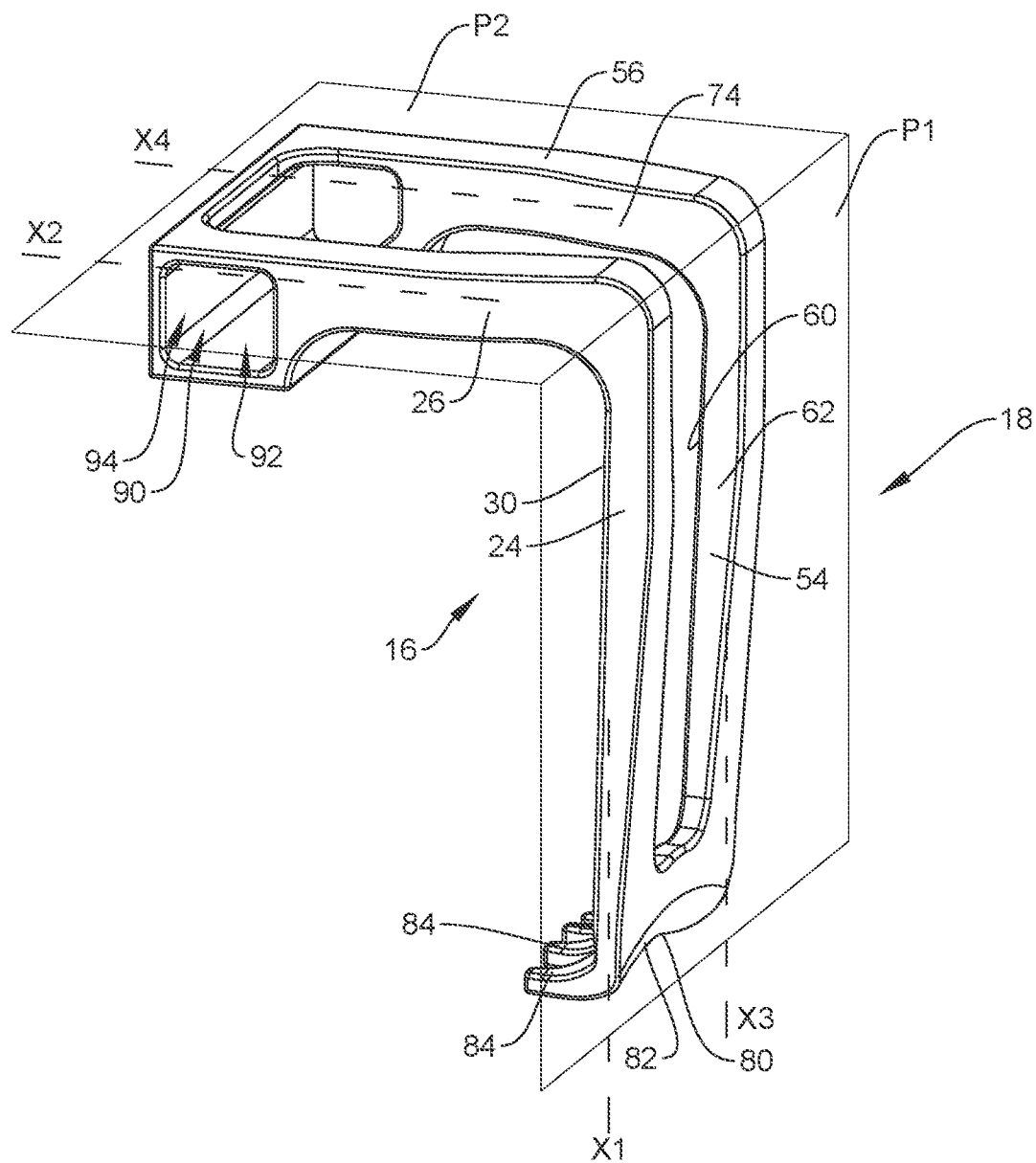
FIG. 2 is a perspective view of the components shown in FIG. 1.

Portion 26 extends along an axis X2 at an angular orientation, such as, for example, perpendicular to axis X1, as shown in FIG. 2. In some embodiments, portion 26 may be oriented in alternate configurations, such as, for example, parallel, co-axial, angularly offset, offset and/or staggered relative to portion 24. Portion 26 extends between an end 40 and an end 42 along axis X2 in a plane P2. In some embodiments, plane P2 is disposed in a medial-lateral orientation relative to patient body B. Portion 26 includes a surface 44 that provides a limit to and/or restricts a range of movement of a surgical instrument to facilitate selective orientation and positioning of the surgical instrument along plane P1.

Surface 46 extends between arms 16, 18 and is configured to position a surgical instrument in a selected orientation along plane P2. In some embodiments, surface 46 extends perpendicular to axes X2, X4, as shown in FIG. 2. In some embodiments, surface 46 may be oriented in alternate configurations, such as, for example, parallel, co-axial, angularly offset, offset and/or staggered relative to axes X2, X4.

In some embodiments, all or only a portion of arm 16 may have various cross-section configurations, such as, for example, arcuate, cylindrical, oblong, rectangular, polygonal, undulating, irregular, uniform, non-uniform, consistent, variable, and/or U-shape. In some embodiments, surface 32, surface 44 and/or surface 46 may have alternate surface configurations, such as, for example, rough, undulating, porous, semi-porous, dimpled, polished and/or textured.

Arm 18 includes a portion 54 and a portion 56. Portion 54 extends between an end 50 and an end 52 parallel to portion 24 along an axis X3 in plane P1. Portion 54 includes a surface 60 configured for engaging and spacing apart tissue. Portion 24 and portion 54 are spaced apart to form an opening 58 along plane P1 for disposal of a surgical instrument in a selected orientation along plane P1. Portion 54 includes a surface 62 that provides a limit to and/or restricts a range of movement of a surgical instrument to facilitate selective orientation and positioning of the surgical instrument along plane P1.

Figure 3:
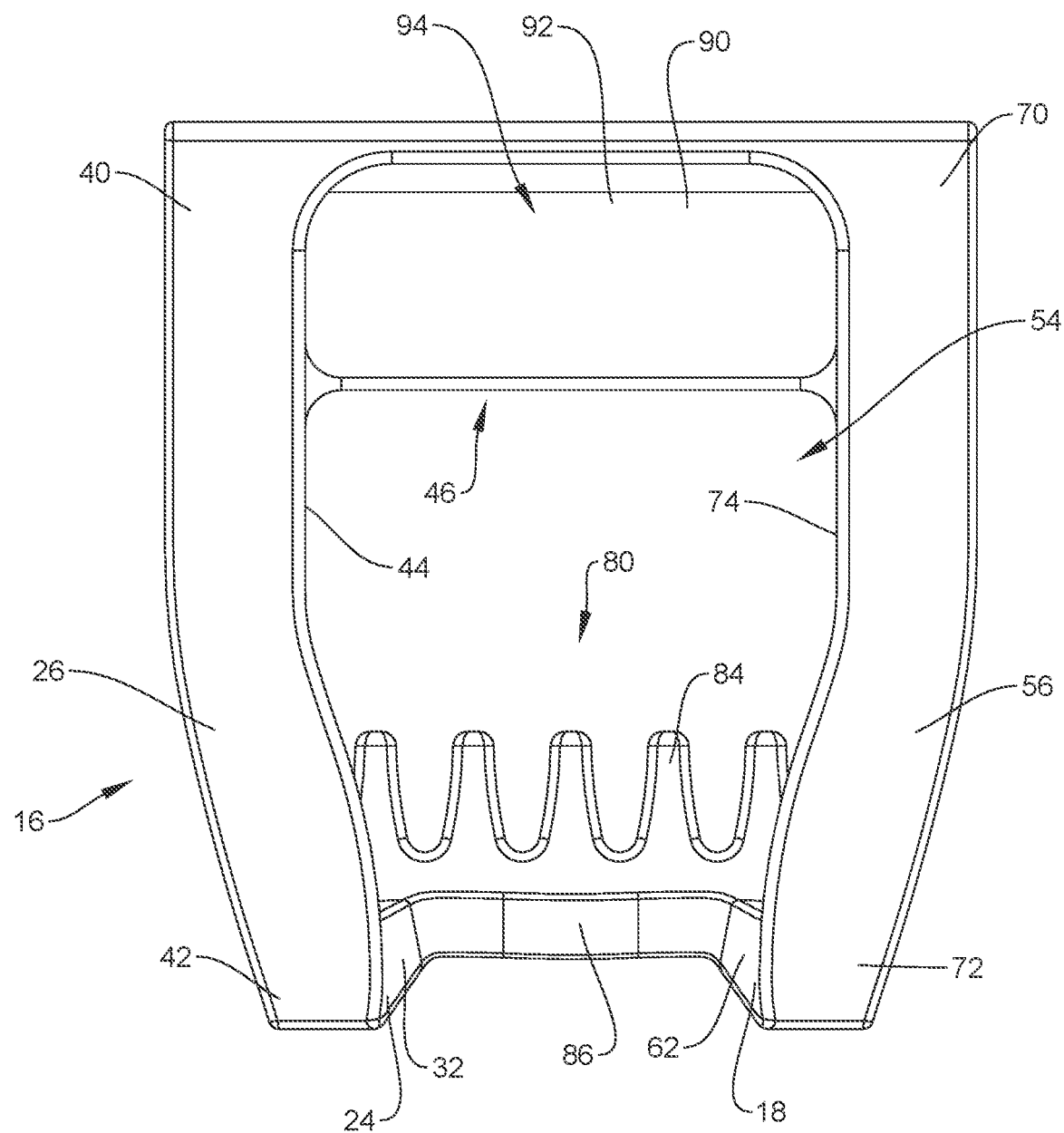
FIG. 3 is a top view of the components shown in FIG. 1.

Portion 56 extends along an axis X4, disposed parallel to axis X2, and at an angular orientation, such as, for example, perpendicular to axis X3, as shown in FIG. 2. In some embodiments, portion 56 may be oriented in alternate configurations, such as, for example, parallel, co-axial, angularly offset, offset and/or staggered relative to portion 54. Portion 56 extends between an end 70 and an end 72 along axis X4 in plane P2, as described herein. Portion 26 and portion 56 are spaced apart to form an opening 59 along plane P2 for disposal of a surgical instrument in a selected orientation along plane P1 and/or P2. Portion 56 includes a surface 74, as shown in FIG. 3, which provides a limit to and/or restricts a range of movement of a surgical instrument to facilitate selective orientation and positioning of the surgical instrument along plane P1. Openings 58, 59 are disposed in communication to facilitate movement of a surgical instrument along planes P1, P2.

In some embodiments, all or only a portion of arm 18 may have various cross-section configurations, such as, for example, arcuate, cylindrical, oblong, rectangular, polygonal, undulating, irregular, uniform, non-uniform, consistent, variable, and/or U-shape. In some embodiments, surface 62 and/or surface 76 may have alternate surface configurations, such as, for example, rough, undulating, porous, semi-porous, dimpled, polished and/or textured.

Blade 14 includes a member 80. Member 80 is connected with ends 22, 52 of arms 16, 18. Member 80 is disposed with arms 16, 18 to support, position, provide a limit and/or restrict a range of movement of a surgical instrument in a selected orientation relative to the surgical site. Member 80 includes a surface 82 having an arcuate configuration. Surface 82 is curved in a convex configuration between ends 22, 52 such that surface 82 provides for anatomical relief of body tissue. In some embodiments, surface 82 facilitates an increase of insertion of retractor 12 into patient body B adjacent to a working surgical field. In some embodiments, surface 82 is configured for insertion with a patient body B without impinging on the facets or the transverse processes. Surface 82 includes a plurality of teeth 84 extending transverse to surface 82, as shown in FIG. 2. Teeth 84 are configured to facilitate capture and/or separation of tissue. Member 80 includes a surface 86 disposed adjacent to surfaces 32, 62 to support, provide a limit and/or restrict a range of movement of a surgical instrument in a selected orientation relative to the surgical site.

Surfaces 32, 44, 62, 74 and/or 86 provide a limit to and/or restrict a range of movement of a surgical instrument to facilitate selective orientation and positioning of the surgical instrument, for example, along a cephalad-caudal direction relative to vertebral tissue within openings 58, 59 along plane P1. For example, the working end of a surgical instrument is engaged with and fixed with vertebral tissue. In some embodiments, the handle end of the surgical instrument is moveable through an angular range of 0 through 60 degrees relative to vertebral tissue along plane P1. In some embodiments, a surgical instrument is moveable through an angular range of 0 through 20 degrees relative to vertebral tissue along plane P1. Contact of a surgical instrument with surfaces 32, 44, 62, 74 and/or 86 provide limits on the range of movement and/or rotation of the surgical instrument through the angular range in plane P1.

Surfaces 46 and/or 86 provide a limit to and/or restrict a range of movement of a surgical instrument to facilitate selective orientation and positioning of the surgical instrument along, for example, a medial-lateral direction relative to the vertebral tissue within openings 58, 59 along plane P2. For example, the working end of the surgical instrument is engaged with and is fixed with vertebral tissue. In some embodiments, the handle end of the surgical instrument is moveable through an angular range of 0 through 40 degrees relative to vertebral tissue within plane P2. In some embodiments, the surgical instrument is moveable through an angular range of 0 through 30 degrees relative to vertebral tissue within plane P2. Contact of a surgical instrument with surfaces 46, 86 provide limits on the range of movement and/or rotation of the surgical instrument through the angular range in plane P2.

Figure 4:
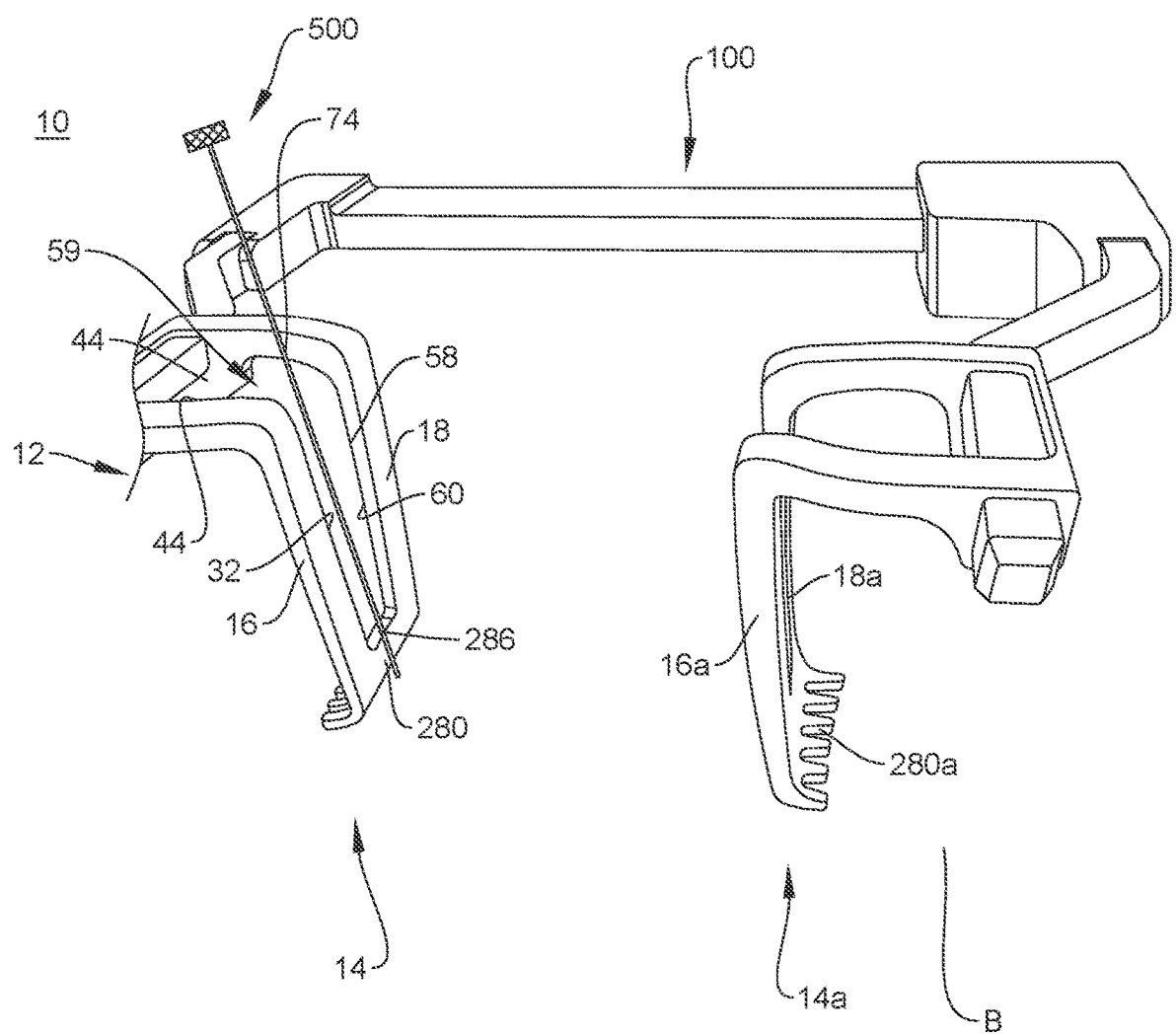
FIG. 4 is a perspective view of components of one embodiment of a system in accordance with the principles of the present disclosure disposed with a patient body.

Ends 40, 70 include a mating portion 90 that extends along surface 46. Portion 90 includes a surface 92 that defines an opening 94. Opening 94 is configured for disposal of jogs 102 of retraction rack 100, as shown in FIG. 4. Blade 14 is attached with rack 100 for relative translation to space apart tissue. In some embodiments, a ratchet mechanism on rack 100 is configured to facilitate retraction of tissue. Blade 14 is attached with a rack 100 such that blade 14 is movable in one or a plurality of degrees of freedom to one or a plurality of orientations relative to rack 100, stationary surgical equipment and/or the patient body B in connection with a surgical procedure. In some embodiments, the degrees of freedom of movement of blade 14 to one or a plurality of orientations relative to rack 100, stationary surgical equipment and/or patient body B can include one or a plurality of degrees of movement in translation, one or a plurality of degrees of movement in rotation, planar movement such as a four bar linkage, spherical movement such as poly-axial and/or joints or links such as a kinematic chain. In some embodiments, the degrees of movement in translation can include up, down, left, right, forward and/or backward. In some embodiments, the degrees of movement in rotation can include tilting, swiveling and/or pivoting in one or a plurality directions. In some embodiments, blade 14 is independently and selectively movable relative to rack 100, stationary surgical equipment and/or patient body B. In some embodiments, one or a plurality of blades 14 may be attachable with rack 100.

In some embodiments, retractor 12 may be employed with various surgical instruments, such as, for example, drivers, extenders, reducers, spreaders, distractors, clamps, forceps, elevators and drills, which may be alternately sized and dimensioned, and arranged as a kit. In some embodiments, surgical system 10 may comprise the use of microsurgical and image guided technologies, such as, for example, surgical navigation components employing emitters and sensors, which may be employed to track introduction and/or delivery of the components of surgical system 10 including the surgical instruments to a surgical site. See, for example, the surgical navigation components and their use as described in U.S. Pat. Nos. 6,021,343, 6,725,080, 6,796,988, the entire contents of each of these references being incorporated by reference herein.

Figure 5:
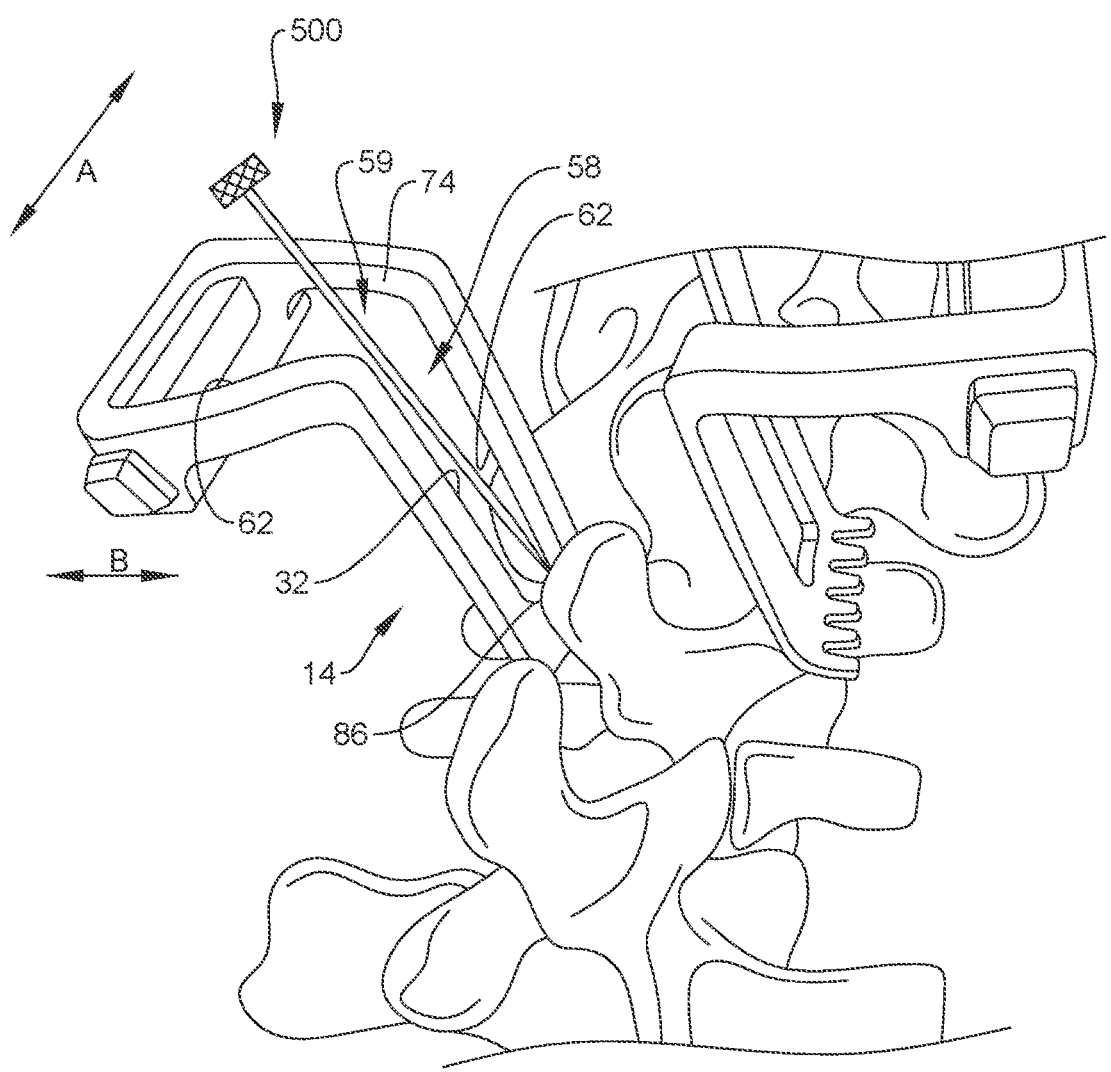
FIG. 5 is a perspective view of components of one embodiment of a system in accordance with the principles of the present disclosure disposed with a patient body.

In assembly, operation and use, surgical system 10, similar to the systems and methods described herein, is employed with a surgical procedure for treatment of a spinal disorder, such as those described herein, affecting a section of a spine of a patient. Surgical system 10 may also be employed with other surgical procedures. In some embodiments, surgical system 10 is employed to implant components, such as bone fasteners, rods, interbody devices and plates, with patient body B, as shown in FIGS. 4 and 5.

With the body disposed in a selected orientation, for example, for a midline posterior TL surgical approach for a contra-lateral decompression and discectomy, a medical practitioner makes and/or creates an incision in tissue, which includes soft tissue and/or muscle, to obtain access to a surgical site including affected vertebral levels of vertebrae V. The tissue is manipulated to space the tissue adjacent to the incision.

Surgical retractor 12, as described herein, is disposed with the incision for spacing tissue. Blades 14, 14a, as described herein, are connected with rack 100. Blades 14, 14a are relatively moveable and configured for insertion sequentially around the intervertebral space. Surfaces 280, 280a are positioned to provide anatomical relief and allow blades 14, 14a to be disposed in the working surgical field without impinging on the facets or the transverse processes, as described herein. Blades 14, 14a are manipulated for movement by rack 100, as described herein, relative to vertebrae V.

Opening 59 is oriented in plane P2 that is disposed in the cephalad-caudal direction of vertebrae V and opening 58 is oriented in plane P1 disposed in a medial-lateral direction relative to vertebrae V. A surgical instrument 500 is inserted through opening 59 and opening 58, as shown in FIG. 4. As surgical instrument 500 is manipulated, contact with surfaces 32, 44, 62, 74 and/or 86 provide a limit to and/or restrict a range of movement of a surgical instrument, as described herein, to facilitate selective orientation and positioning of surgical instrument 500 in the cephalad-caudal direction, as shown by arrows A in FIG. 5, within opening 59 and opening 58.

As surgical instrument 500 is manipulated, contact with surfaces 46 and/or 86 provide a limit to and/or restrict a range of movement of surgical instrument 500 in the medial-lateral direction within opening 59 and opening 58, as shown by arrows B in FIG. 5. Surgical instrument 500 is moveable through an angular range of 0 through 30 degrees relative to vertebrae V along the medial-lateral direction of vertebrae V. Surgical instrument 500 is moveable through an angular range of 0 through 20 degrees relative vertebrae V along the cephalad-caudal direction of vertebrae V.

In some embodiments, pilot holes or the like are made in vertebrae V adjacent the intervertebral space for receiving bone fasteners and/or attaching spinal constructs, which may include rods and plates. An inserter is attached with the implants and/or spinal constructs for delivery adjacent to a surgical site for implantation adjacent one or more vertebra and/or intervertebral spaces of the vertebral levels.

Upon completion of a procedure, as described herein, the surgical instruments, assemblies and non-implanted components of surgical system 10 are removed and the incision(s) are closed. One or more of the components of surgical system 10 can be made of radiolucent materials such as polymers. Radiopaque markers may be included for identification under x-ray, fluoroscopy, CT or other imaging techniques. In some embodiments, the use of surgical navigation, microsurgical and image guided technologies, as described herein, may be employed to access, view and repair spinal deterioration or damage, with the aid of surgical system 10. In some embodiments, surgical system 10 may include implants and/or spinal constructs, which may include one or a plurality of plates, rods, connectors and/or bone fasteners for use with a single vertebral level or a plurality of vertebral levels.

Figure 6:
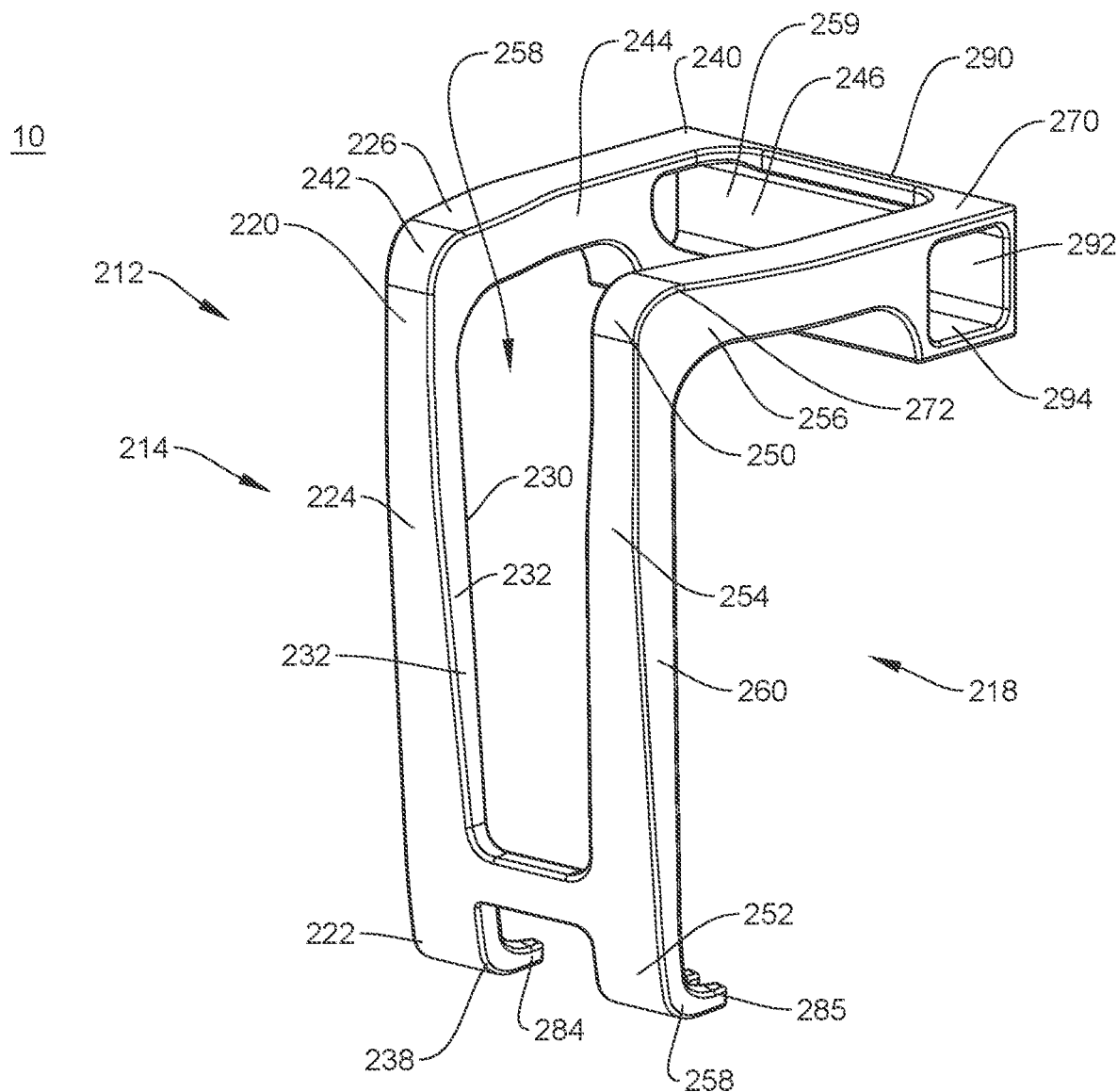
FIG. 6 is a perspective view of components of one embodiment of a surgical system in accordance with the principles of the present disclosure.

In one embodiment, as shown in FIGS. 6-11, surgical system 10, similar to the systems and methods described herein, includes a retractor 220, similar to retractor 12 described herein, and includes a blade 214. Blade 214 includes an arm 216 and an arm 218 being spaced apart from arm 216 forming an opening 217 to guide the surgical instrument along the selected orientation, as shown in FIG. 6. Arm 216 includes a portion 224 and a portion 226. Portion 224 extends between an end 220 and an end 222 in plane P1, similar to portion 24 described herein. Portion 224 includes a surface 230 configured for engaging and spacing apart tissue. Portion 224 includes a surface 232 that provides a limit to and/or restricts a range of movement of a surgical instrument to facilitate selective orientation and positioning of the surgical instrument along plane P1, similar to surface 32 described herein. End 222 includes a distal tip 238 having an arcuate configuration angled to capture and/or separate tissue. Tip 238 includes a plurality of teeth 284, as shown in FIG. 6. Teeth 284 are configured to facilitate capture and/or separation of tissue.

Portion 226 extends between an end 240 and an end 242 along plane P2, similar to portion 26 described herein. Portion 226 includes a surface 244. Surface 244 that provides a limit to and/or restricts a range of movement of a surgical instrument to facilitate selective orientation and positioning of the surgical instrument along plane P1, similar to that described herein. Surface 246, similar to surface 46 described herein, extends between arms 216, 218 and provides a limit to and/or restricts a range of movement of a surgical instrument to facilitate selective orientation and positioning of the surgical instrument along plane P2, similar to surface 46 described herein.

Arm 218 includes a portion 254 and a portion 256. Portion 254 extends between an end 250 and an end 252 in plane P1 and is disposed parallel to portion 224. Portion 254 includes a surface 260 configured for engaging and spacing apart tissue. Portion 254 includes a surface 262 that provides a limit to and/or restricts a range of movement of a surgical instrument to facilitate selective orientation and positioning of the surgical instrument along plane P1, similar to surface 62 described herein. End 252 includes a distal tip 258 having an arcuate configuration angled to capture and/or separate tissue. Tip 258 includes a plurality of teeth 285, as shown in FIG. 6. Teeth 285 are configured to facilitate capture and/or separation of tissue. Portion 224 and portion 254 are spaced apart to form an opening 257 disposed along plane P1 for disposal of a surgical instrument along a selected orientation in plane P1, similar to opening 58 described herein.

Portion 256 extends between an end 270 and an end 272, similar to portion 56 described herein. Portion 256 includes a surface 274, as shown in FIG. 6. Surface 274 and surface 262 are configured to position a surgical instrument in a selected orientation within plane P1, as described herein. Surface 246 provides a limit to and/or restricts a range of movement of a surgical instrument to facilitate selective orientation and positioning of the surgical instrument along plane P2. Portion 226 and portion 256 are spaced apart to form an opening 259 disposed along plane P2 for disposal of the surgical instrument along the selected orientation in plane P1 and/or P2, similar to opening 59 described herein.

Figure 7:
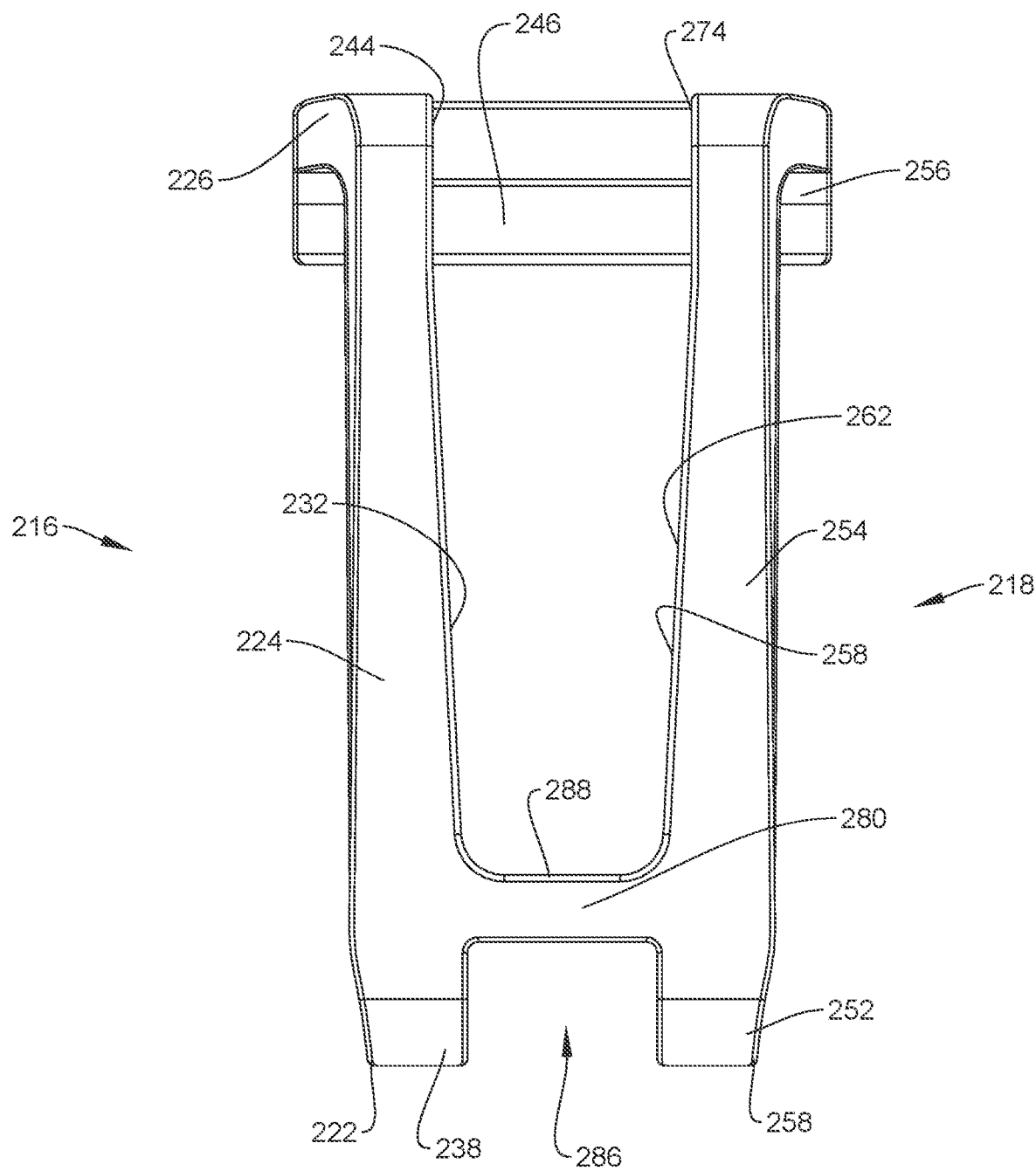
FIG. 7 is a side view of the components shown in FIG. 6.
Figure 8:
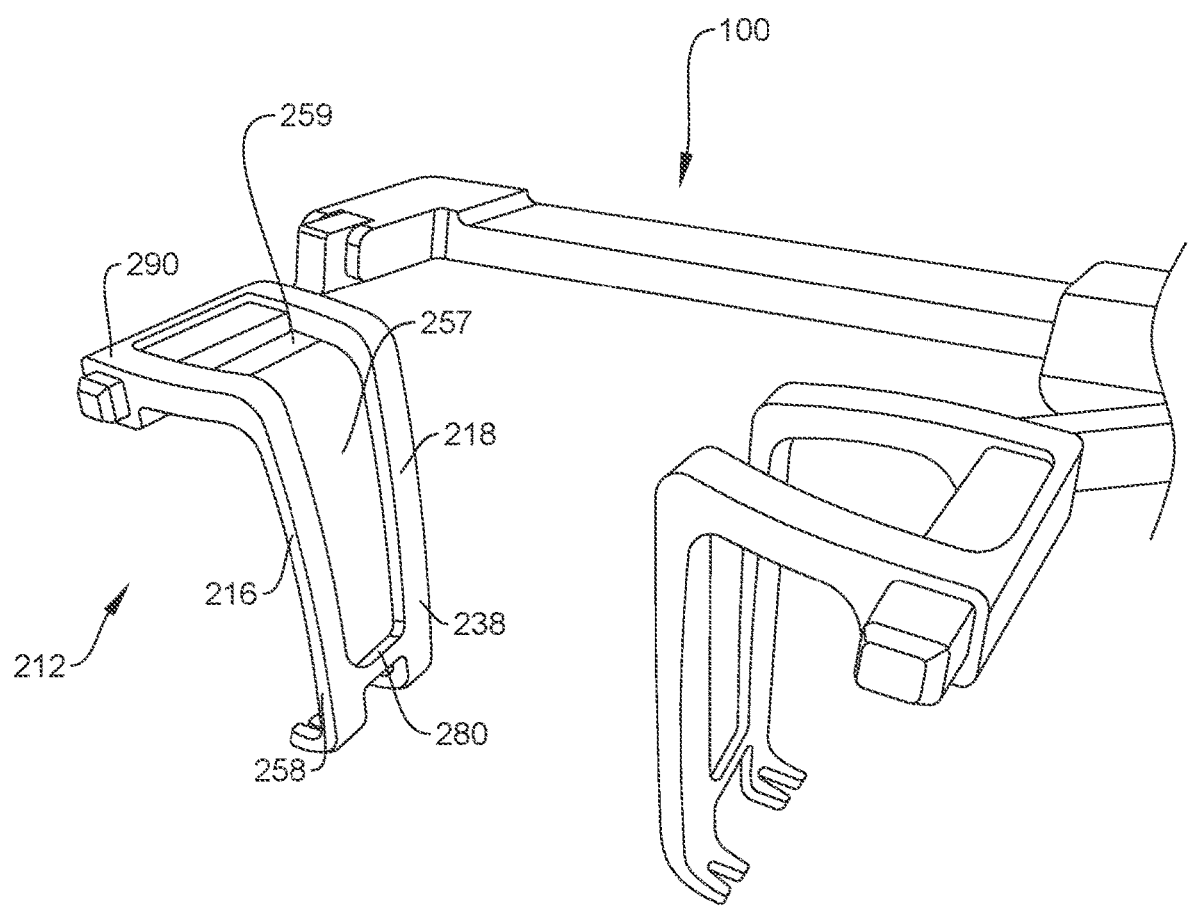
FIG. 8 is a perspective view of components of one embodiment of a system in accordance with the principles of the present disclosure disposed with a patient body.
Figure 9:
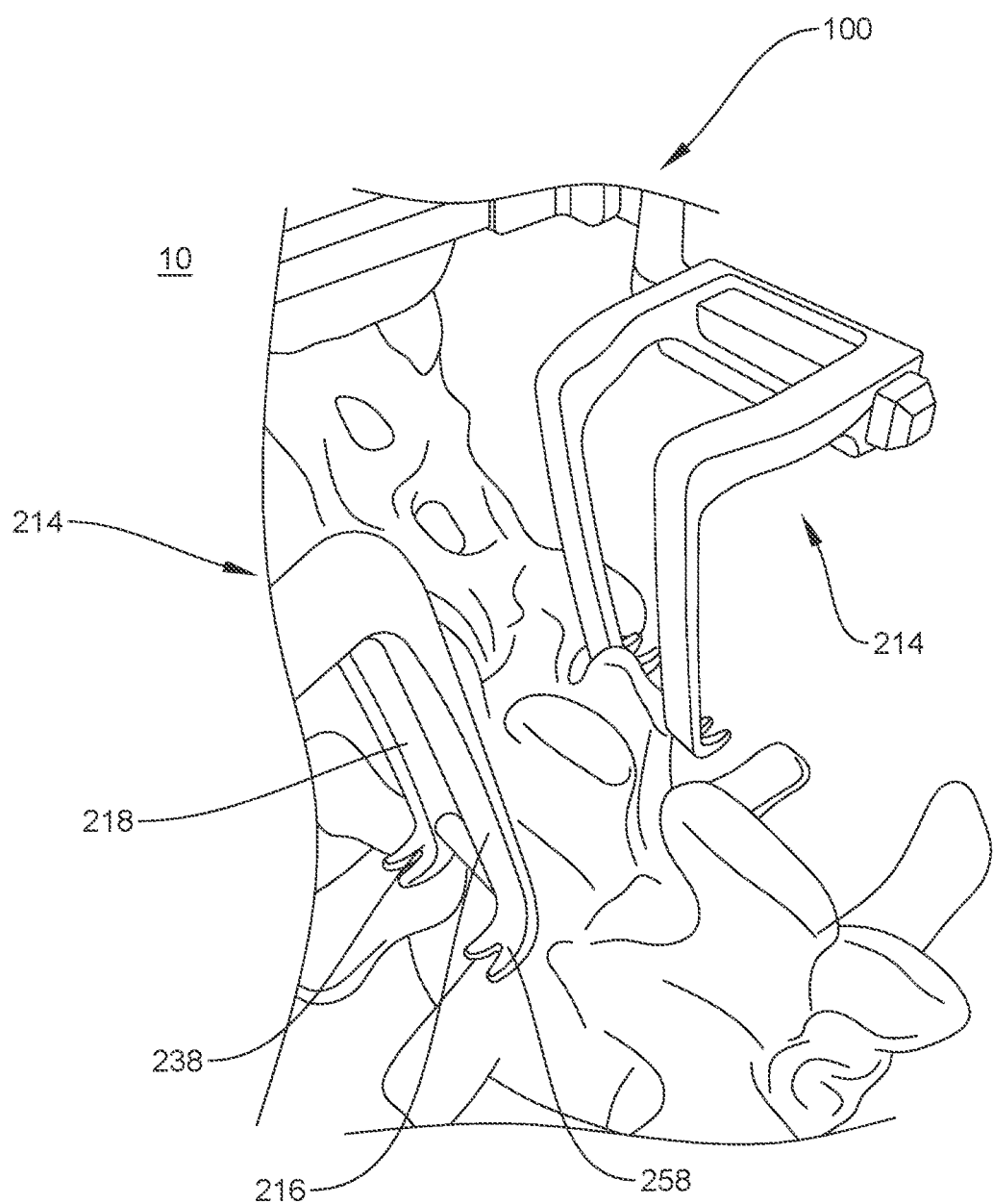
FIG. 9 is a perspective view of components of one embodiment of a system in accordance with the principles of the present disclosure disposed with a patient body.

Blade 214 includes a member 280, similar to member 80 described herein. Member 280 is connected with arms 216, 218. Member 280 is disposed substantially perpendicular relative to arms 216, 218, as shown in FIG. 7. Member 280 is disposed a distance from tips 238, 258 forming a cutout 286. Cutout 286 provides for anatomical relief and facilitates an increase of insertion of retractor 212 into patient body B adjacent to a working surgical field, as described herein. Cutout 286 is configured to resist and/or prevent impinging the facets or the transverse processes. Member 280 includes a surface 288 disposed adjacent to surfaces 232, 262 to provide a limit to and/or restrict a range of movement of a surgical instrument to facilitate selective orientation and positioning of the surgical instrument in the selected orientation relative to the surgical site.

Ends 240, 270 include a mating portion 290 that extends along surface 246, as described herein. Portion 290 includes a surface 292 that defines an opening 294. Opening 294 is configured for disposal of a retraction rack 100, as described herein.

Figure 10:
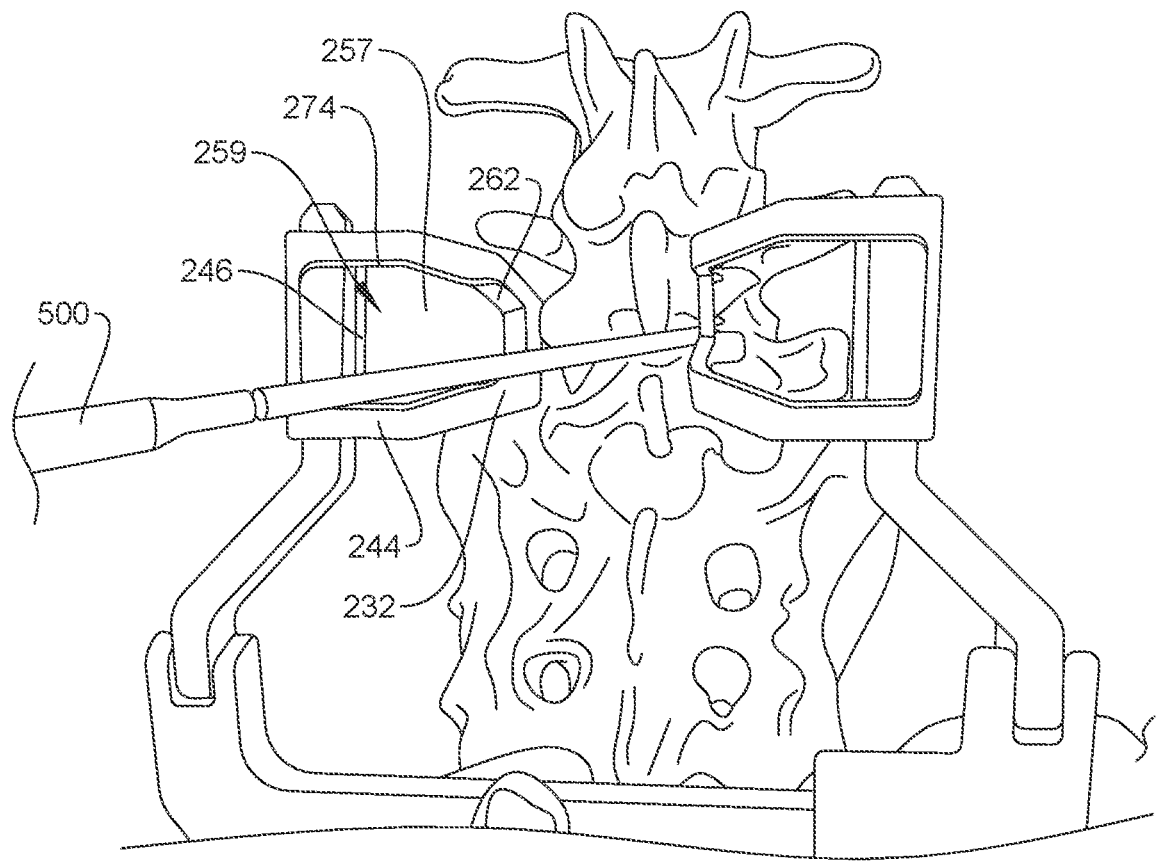
FIG. 10 is a plan view of components of one embodiment of a system in accordance with the principles of the present disclosure disposed with a patient body.

In use, as shown in FIGS. 8-11, as surgical instrument 500 is manipulated, contact with surfaces 232, 244, 262, 274 and/or 288 provide a limit and/or restriction to a range of movement of surgical instrument 500 for disposal in a selected orientation, for example, a cephalad-caudal direction relative to vertebral tissue, within openings 257, 259 along plane P1. For example, a working end of surgical instrument 500 is engaged with and fixed with vertebrae V. A handle end of surgical instrument 500 is moveable through an angular range of 0 through 20 degrees relative to vertebrae V within plane P1, as shown in FIG. 10. Contact with surfaces 232, 244, 262, 274 and/or 288 provide limits on the range of movement and/or rotation of surgical instrument 500 through the angular range in plane P1.

Figure 11:
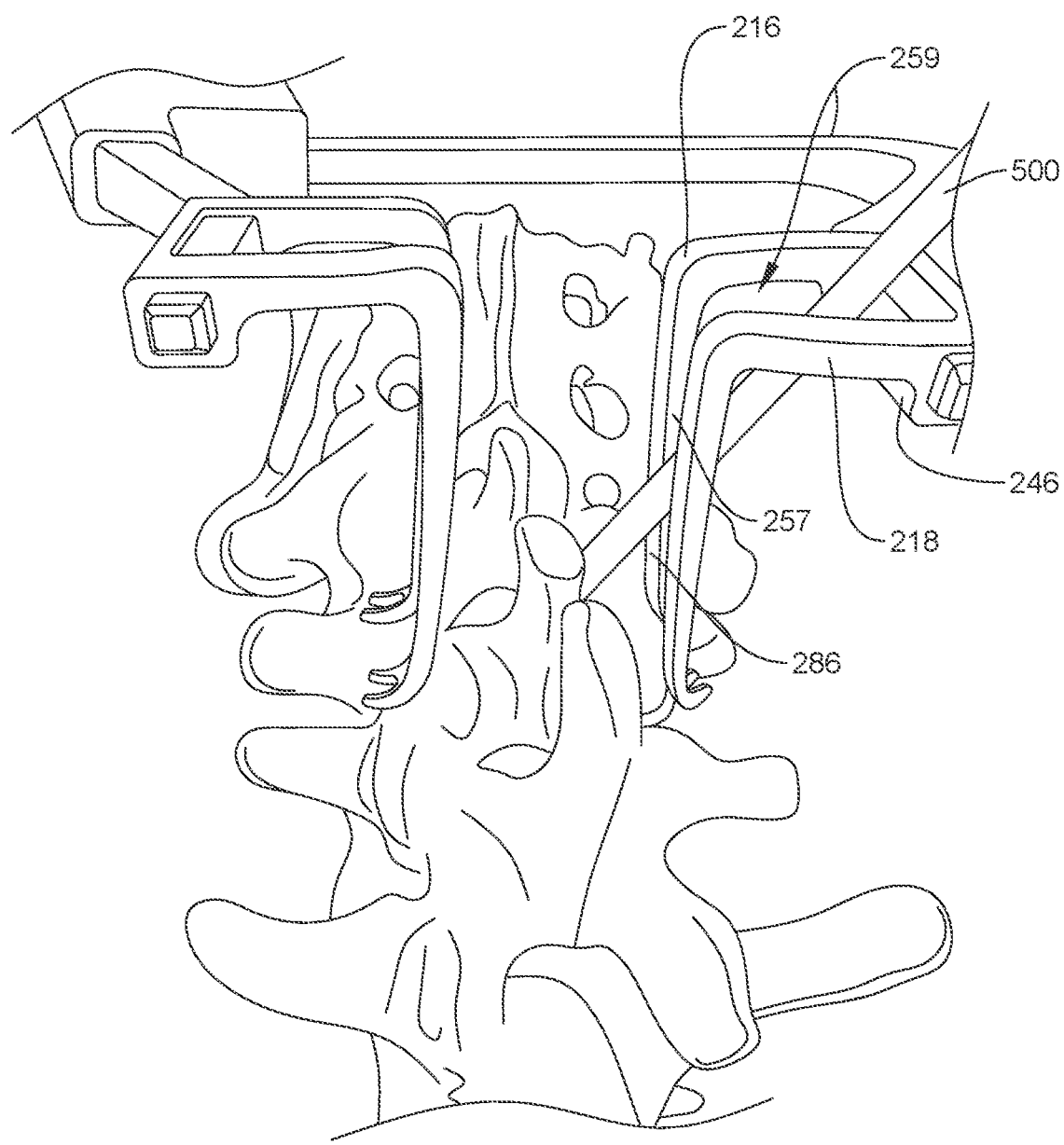
FIG. 11 is a perspective view of components of one embodiment of a system in accordance with the principles of the present disclosure disposed with a patient body.

As surgical instrument 500 is manipulated, contact with surfaces 246 and/or 288 provide a limit and/or restriction on a range of movement of surgical instrument 500 for disposal in a selected orientation, for example, a medial-lateral direction relative to vertebral tissue within openings 257, 259 along plane P2. For example, surgical instrument 500 is fixed with vertebrae V and is moveable through an angular range of 0 through 30 degrees relative to vertebrae V along plane P2, as shown in FIG. 11. Contact with surfaces 246 and 288 provide limits on the range of movement and/or rotation of the surgical instrument through the angular range in plane P2.

Figure 12:
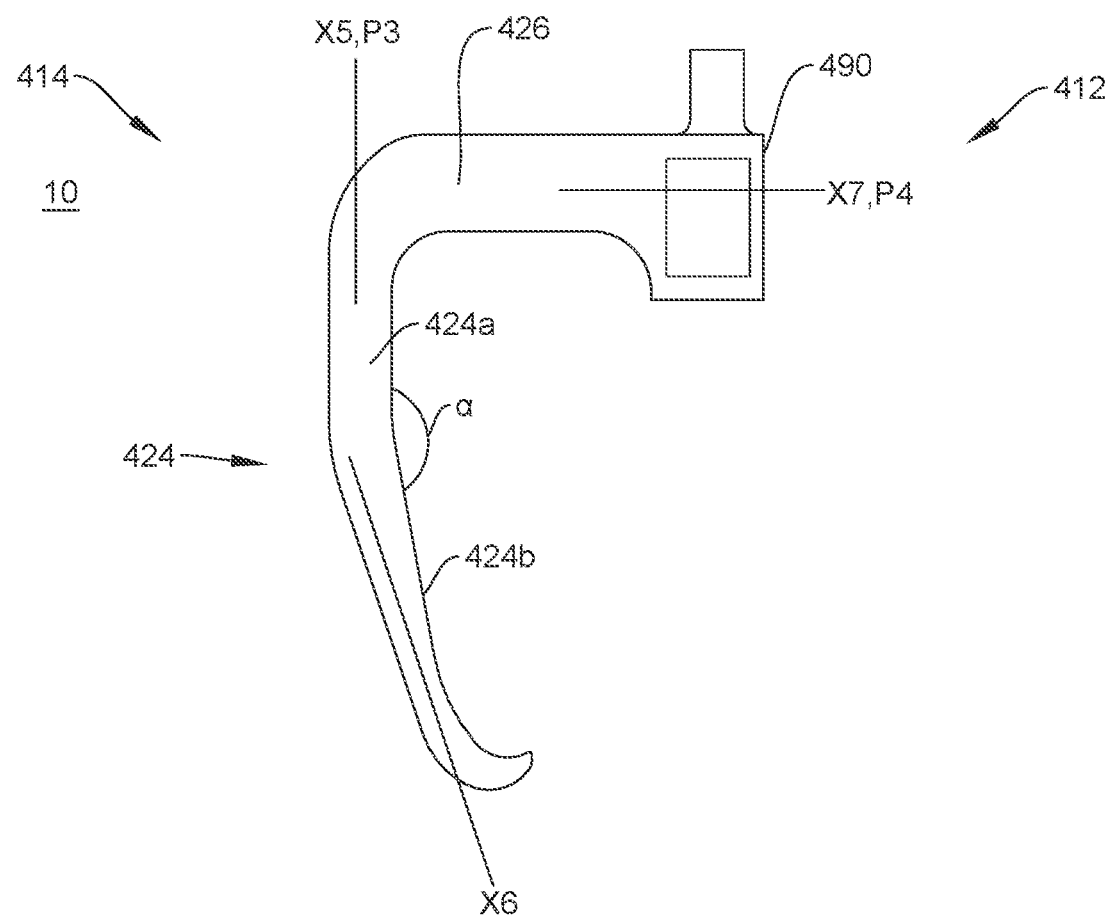
FIG. 12 is a side view of components of one embodiment of a surgical system in accordance with the principles of the present disclosure.
Figure 13:
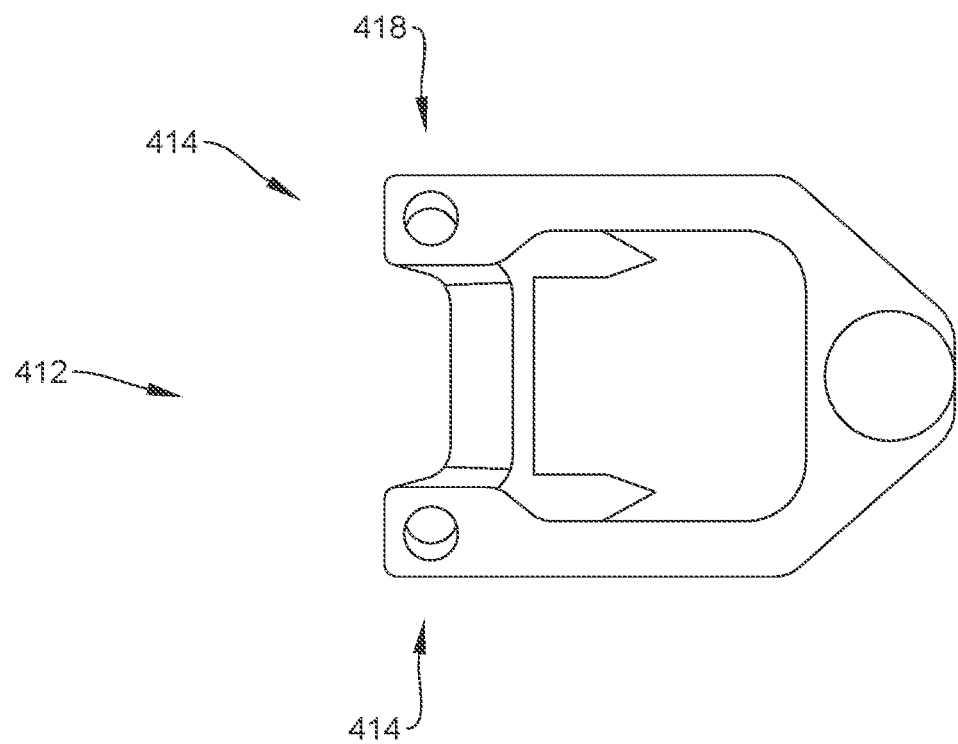
FIG. 13 is a top view of the components shown in FIG. 12.

In one embodiment, as shown in FIGS. 12 and 13, surgical system 10, similar to the systems and methods described herein, includes a retractor 412, similar to retractor 12 described herein. Retractor 412 includes a blade 414 for, similar to blade 14 described herein. Blade 414 is configured to provide selective orientation and positioning of a surgical instrument and/or support of patient anatomy, as described herein.

Blade 414 includes an arm 416 and an arm 418 being spaced apart from arm 416, as shown in FIG. 13. Arm 416 includes a portion 424 and a portion 426. Portion 424 includes a section 424a and a second 424b. Section 424a extends along an axis X5 in a plane P3. In some embodiments, plane P3 is disposed a cephalad-caudad orientation relative to a patient body B. Section 424b extends along an axis X6. Axis X6 is disposed at an angle a relative to axis X5 and/or plane P3. In some embodiments, angle a is configurated as an obtuse angle, as shown in FIG. 12. In some embodiments, angle a may be acute or perpendicular. In some embodiments, section 424b may be oriented in alternate configurations, such as, for example, parallel, co-axial, angularly offset, offset and/or staggered relative to section 424a. The angular orientation of section 424b to section 424a is configured to increase purchase of blade 414 with tissue. In some embodiments, the angular orientation of section 424b to section 424a is configured to maximize working space distally and resists and/or prevents impingement on bony anatomy, such as, for example, facets or transverse processes.

Figure 14:
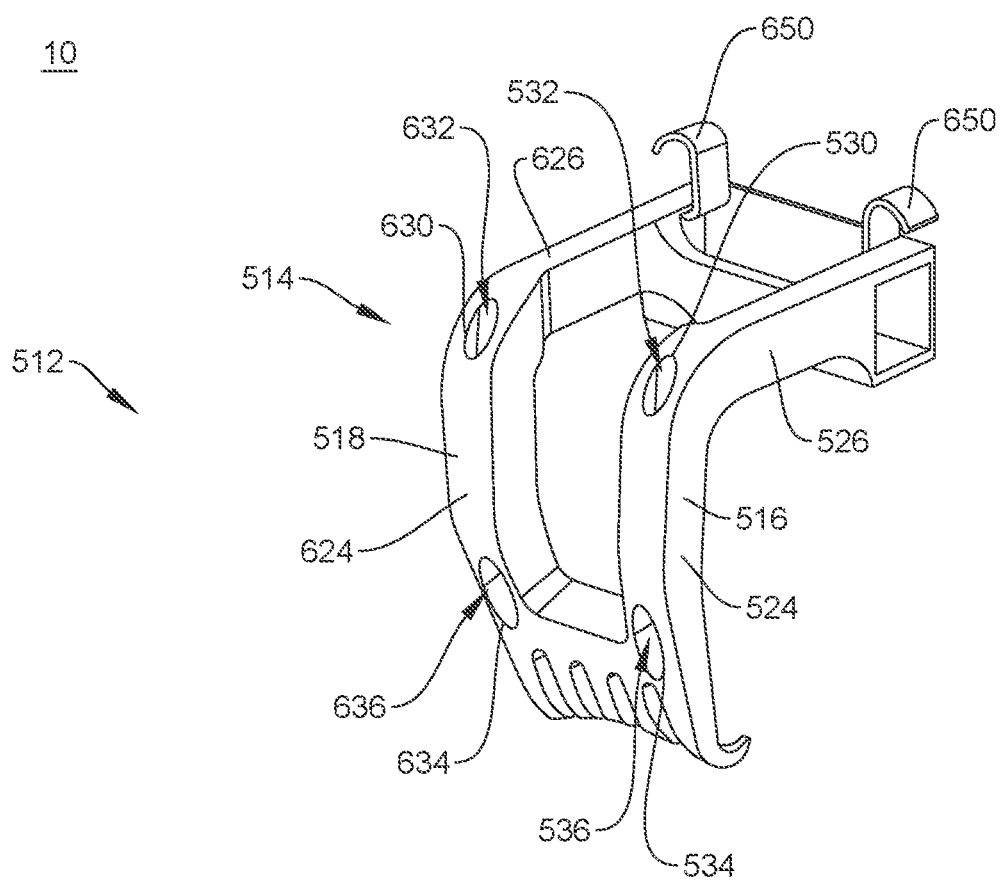
FIG. 14 is a perspective view of components of one embodiment of a surgical system in accordance with the principles of the present disclosure.
Figure 15:
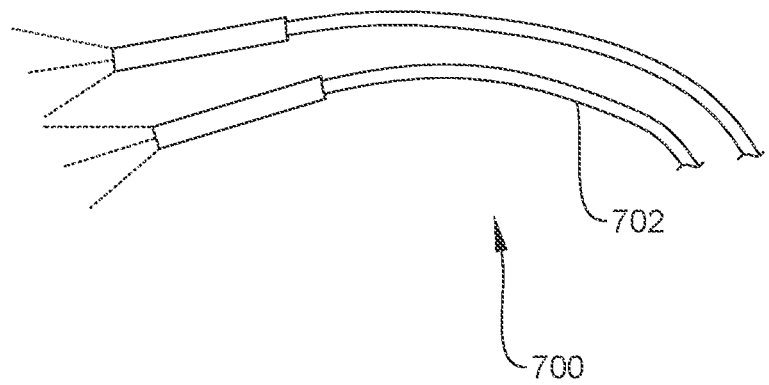
FIG. 15 side view of a component of a surgical system in accordance with the principles of the present disclosure.

In one embodiment, as shown in FIGS. 14 and 15, surgical system 10, similar to the systems and methods described herein, includes a retractor 512, similar to retractor 12 described herein. Retractor 512 includes a blade 514 for, similar to blade 14 described herein. Blade 514 is configured to provide selective orientation and positioning of a surgical instrument and/or support of patient anatomy, as described herein.

Blade 514 includes an arm 516 and an arm 518 being spaced apart from arm 516, as shown in FIG. 14. Arm 516 includes a portion 524, similar to portion 24 and a portion 526, similar to portion 26, as described herein. Portion 524 includes a surface 530 that defines an opening 532 and an opening 534. A channel 536 extends between openings 532, 534. Channel 536 is configured for disposal of a light source 700, as shown in FIG. 15. Light source 700 is guided through channel 536 to provide light to the working space at the surgical site.

Arm 518 includes a portion 624, similar to portion 24 and a portion 626, similar to portion 26, as described herein. Portion 624 includes a surface 630 that defines an opening 632 and an opening 634. A channel 536 extends between openings 632, 634. Channel 536 is configured for disposal of light source 700, as described herein.

Portion 526 and portion 626 each include a flange, such as, for example, a hook 650, as shown in FIG. 14. Hooks 650 are configured to facilitate organization of extensions and/or cables 702 extending from light source 700. In some embodiments, hooks 650 are configured to resist and/or prevent cables 702 from obstructing visualization the surgical site and/or the ability to operate in the working space.

It will be understood that various modifications and/or combinations may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical retractor comprising:
a longitudinal element extending along a longitudinal axis between opposite first and second ends;
a first extension coupled to the first end;
a second extension coupled to the second end such that the second extension is configured to slide linearly relative to the longitudinal element along the longitudinal axis;
a first blade including a first arm and a second arm, proximal ends of the first and second arms being coupled to the first extension, distal ends of the first and second arms being connected by a member, the first arm being spaced apart from the second arm between the first extension and the member, the member being disposed with the first and second arms to support at least one surgical instrument in a selected orientation relative to a surgical site; and
a second blade coupled to the second extension,
wherein the first blade and the second blade are radiolucent.

2. A surgical retractor as recited in claim 1, wherein:
the first arm includes a first portion and a second portion disposed at an angular orientation relative to the first portion of the first arm;
the second arm includes a first portion and a second portion disposed at an angular orientation relative to the first portion of the second arm; and
the first portions of the first and second arms define a first plane and the second portions of the first and second arms define a second plane disposed at a perpendicular orientation relative to the first plane.

3. A surgical retractor as recited in claim 1, wherein the member includes a linear configuration.

4. A surgical retractor as recited in claim 1, wherein the member includes an arcuate configuration.

5. A surgical retractor as recited in claim 1, wherein the member includes a plurality of teeth.

6. A surgical retractor as recited in claim 1, wherein the member is coupled to tips of the distal ends of the first and second arms.

7. A surgical retractor as recited in claim 1, wherein the second extension is slidable relative to the first extension in opposite directions along a length of the longitudinal element.

8. A surgical retractor as recited in claim 1, wherein the first extension is fixed relative to the longitudinal element and the second extension is slidable along the longitudinal element.

9. A surgical retractor as recited in claim 1, wherein the first extension includes a first portion that is coupled directly to the longitudinal element and a second portion that is offset relative to the first portion, the first blade being coupled to the second portion, the second extension being slidable along the longitudinal element.

10. A surgical retractor as recited in claim 1, wherein the first and second extensions each include a linear first portion, a linear second portion and a linear third portion, the second portion being positioned between the first portion and the third portion, the first portion being coupled directly to the longitudinal element, the first portion and the third portion extending perpendicular to the longitudinal element, the second portion extending at an acute angle relative to the longitudinal element.

11. A surgical retractor as recited in claim 1, wherein the member includes teeth, the second extension being movable relative to the first extension along the longitudinal element between a first orientation in which the first blade is spaced apart from the second blade and a second orientation in which the first blade directly engages the second blade, the teeth of the member being spaced apart from the second blade when the second extension is in the second orientation.

12. A surgical retractor as recited in claim 1, wherein the first extension includes a linear first portion, a linear second portion and a linear third portion, the second portion being positioned between the first portion and the third portion, the first portion being coupled directly to the longitudinal element, the first and second arms being coupled directly to the third portion, the first portion and the third portion extending perpendicular to the longitudinal element, the second portion extending at an acute angle relative to the longitudinal element.

13. A surgical retractor as recited in claim 1, wherein the first arm is spaced apart from the second arm by an opening that extends from the extension to the member.

14. A surgical retractor as recited in claim 1, wherein the first blade is monolithic.

15. A surgical retractor as recited in claim 1, wherein the first extension is fixed relative to the longitudinal element.

16. A surgical retractor as recited in claim 1, wherein the longitudinal element is free of teeth.

17. A surgical retractor as recited in claim 1, wherein the proximal ends of the first and second arms each extend parallel to the longitudinal element and the distal ends of the first and second arms each extend perpendicular to the longitudinal element, the first arm being spaced apart from the second arm between the extension and the member to define an opening that extends between the proximal ends and the distal ends of the first and second arms.

18. A surgical retractor as recited in claim 1, wherein the first and second arms each further include a first portion and a second portion disposed at an angular orientation relative to the first portion, the first portion of each of the first and second arms directly engaging the longitudinal element and defining a first plane, the second portion of each of the first and second arms defining a second plane disposed at a perpendicular orientation relative to the first plane, the member including a plurality of teeth, at least a portion of each of the teeth being disposed in a third plane, the third plane being parallel to the first plane.

19. A surgical retractor comprising:
a longitudinal element extending along a longitudinal axis between opposite first and second ends;
a first extension coupled to the first end such that the first extension is fixed relative to the longitudinal element along the longitudinal axis;
a second extension coupled to the second end such that the second extension is configured to slide linearly relative to the longitudinal element in opposite directions along the longitudinal axis;
a first blade including a first arm and a second arm, proximal ends of the arms being coupled to the first extension, distal ends of the first and second arms being connected via a member, the first arm being spaced apart from the second arm from the first extension to the member, the member and the first and second arms being relatively disposed in a configuration to guide at least one surgical instrument in a selected orientation relative to a surgical site; and
a second blade coupled to the second extension such that the second blade is movable relative to the first blade, the second blade including spaced apart arms being connected via a member, the member of the second blade and the spaced apart arms of the second blade being relatively disposed in a configuration to guide at least one surgical instrument in a selected orientation relative to the surgical site,
wherein the first blade and the second blade are radiolucent.

20. A surgical system comprising:
a longitudinal element extending along a longitudinal axis between opposite first and second ends;
a first extension coupled to the first end such that the first extension is fixed relative to the longitudinal element along the longitudinal axis and is pivotable relative to the longitudinal element about a pivot axis that extends parallel to the longitudinal axis;
a second extension comprising a housing having the second end disposed therein such that the second extension is configured to slide linearly relative to the longitudinal element in opposite directions along the longitudinal axis;
a first blade including a first arm and a second arm, proximal ends of the first and second arms being coupled to the first extension, distal ends of the first and second arms being connected by a member, the first arm being spaced apart from the second arm from the first extension to the member to define an opening;
a second blade coupled to the second extension,
wherein the first blade and the second blade are radiolucent; and
at least one surgical instrument being supported by the member and disposable within the opening in a selected orientation relative to a surgical site.

* * * * *